United States Patent
Graca et al.

(10) Patent No.: US 9,408,645 B2
(45) Date of Patent: Aug. 9, 2016

(54) INTRAMEDULLARY NAIL LOCKING HOLE ARRANGEMENT

(75) Inventors: Claudia Graca, Kiel (DE); Annika Homeier, Kiel (DE); Ilan Howling, Kiel (DE); Edgar Kaiser, Probsteierhagen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 1 day.

(21) Appl. No.: 14/343,875

(22) PCT Filed: Sep. 16, 2011

(86) PCT No.: PCT/EP2011/004657
§ 371 (c)(1),
(2), (4) Date: Nov. 25, 2014

(87) PCT Pub. No.: WO2013/037386
PCT Pub. Date: Mar. 21, 2013

(65) Prior Publication Data
US 2015/0080893 A1    Mar. 19, 2015

(51) Int. Cl.
*A61B 17/72* (2006.01)
*A61B 17/17* (2006.01)
*A61B 19/00* (2006.01)
*A61B 5/06* (2006.01)

(52) U.S. Cl.
CPC ......... *A61B 17/7233* (2013.01); *A61B 17/1707* (2013.01); *A61B 17/1725* (2013.01); *A61B 17/72* (2013.01); *A61B 19/54* (2013.01); *A61B 5/06* (2013.01)

(58) Field of Classification Search
USPC .................................... 606/62–68
See application file for complete search history.

(56) References Cited

U.S. PATENT DOCUMENTS

| | | | |
|---|---|---|---|
| 4,475,545 A | 10/1984 | Ender | |
| 5,041,115 A | 8/1991 | Frigg et al. | |
| 5,127,913 A * | 7/1992 | Thomas, Jr. | ....... A61B 17/1707 606/62 |
| 5,411,503 A | 5/1995 | Hollstien et al. | |
| 5,584,838 A | 12/1996 | Rona et al. | |
| 5,879,352 A | 3/1999 | Filoso et al. | |
| 6,120,504 A | 9/2000 | Brumback et al. | |
| 6,270,499 B1 | 8/2001 | Leu et al. | |

(Continued)

FOREIGN PATENT DOCUMENTS

| CN | 100534399 C | 9/2009 |
|---|---|---|
| EP | 1382308 A2 | 1/2004 |

(Continued)

OTHER PUBLICATIONS

International Search Report and Written Opinion for Application No. PCT/EP2011/004657 dated Jun. 13, 2012.

(Continued)

*Primary Examiner* — Nicholas Plionis
(74) *Attorney, Agent, or Firm* — Lerner, David, Littenberg, Krumholz & Mentlik, LLP

(57) ABSTRACT

An intramedullary nail has a driving end portion and a non-driving end portion with a longitudinal axis. The non-driving end portion comprises a locking hole arrangement with a sequence of four holes, i.e. spaced from non-driving to driving end a first hole, a second hole, a third hole, and a fourth hole. The first hole and the fourth hole have a corresponding first orientation and the second hole and the third hole have a corresponding second orientation.

20 Claims, 3 Drawing Sheets

(56) References Cited

U.S. PATENT DOCUMENTS

| | | |
|---|---|---|
| 6,461,360 B1 | 10/2002 | Adam |
| 6,547,791 B1 | 4/2003 | Buhren et al. |
| 6,579,294 B2 | 6/2003 | Robioneck |
| 6,616,670 B2 | 9/2003 | Simon et al. |
| 6,666,670 B1 | 12/2003 | Hartman et al. |
| 7,232,443 B2 | 6/2007 | Zander et al. |
| 7,247,156 B2 | 7/2007 | Ekholm et al. |
| 7,247,157 B2 | 7/2007 | Prager et al. |
| 7,686,818 B2 | 3/2010 | Simon et al. |
| 7,771,428 B2 | 8/2010 | Siravo et al. |
| 7,890,179 B2 | 2/2011 | Wiegmann et al. |
| 7,947,043 B2 | 5/2011 | Mutchler |
| 8,083,742 B2 | 12/2011 | Martin |
| 2007/0016203 A1 | 1/2007 | Schlienger et al. |
| 2007/0123878 A1 | 5/2007 | Shaver et al. |
| 2008/0009869 A1 | 1/2008 | Schlienger et al. |
| 2008/0170473 A1 | 7/2008 | Kaiser et al. |
| 2008/0269751 A1 | 10/2008 | Matityahu |
| 2009/0062796 A1 | 3/2009 | Parks et al. |
| 2012/0226094 A1* | 9/2012 | Ritchey ............... A61B 17/1707 600/12 |
| 2012/0226326 A1* | 9/2012 | Overes ................. A61B 17/72 606/329 |

FOREIGN PATENT DOCUMENTS

| | | |
|---|---|---|
| JP | 2002521121 A | 7/2002 |
| JP | 2004-130094 A | 4/2004 |
| WO | 2008086501 A2 | 7/2008 |
| WO | 2010028046 A1 | 3/2010 |

OTHER PUBLICATIONS

Chinese Office Action for Application No. 201180073503.6 dated Jul. 17, 2015.

European Examination for Application No. 11761010.5 dated Jul. 1, 2015.

\* cited by examiner

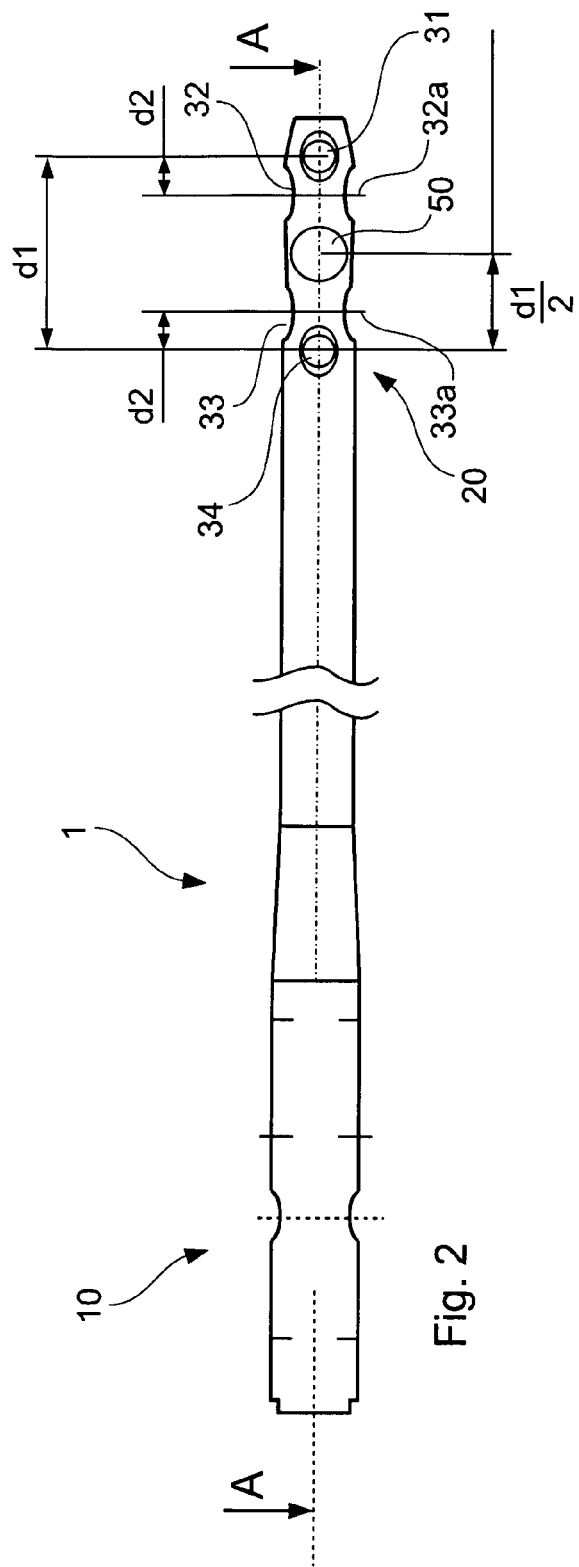
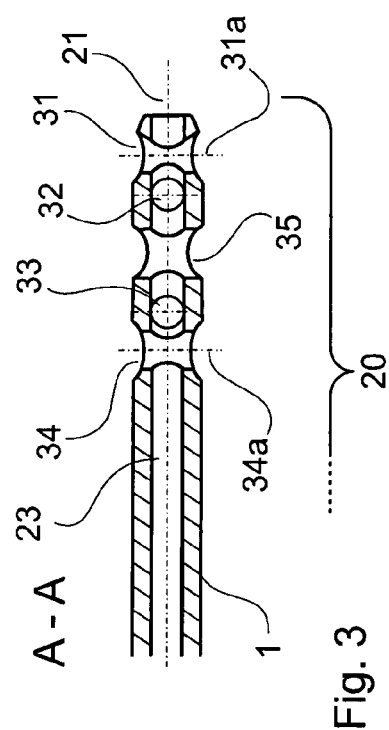
Fig. 2
Fig. 3

INTRAMEDULLARY NAIL LOCKING HOLE ARRANGEMENT

CROSS-REFERENCE TO RELATED APPLICATIONS

The present application is a national phase entry under 35 U.S.C. §371 of International Application No. PCT/EP2011/004657 filed Sep. 16, 2011, published on Mar. 21, 2013 as WO 2013/037386, all of which are hereby incorporated herein by reference.

BACKGROUND OF THE INVENTION

The invention generally relates to an intramedullary nail. Particularly, the invention relates to a locking hole arrangement provided at a non-driving end portion of an intramedullary nail, wherein this end portion of the nail is adapted to be positioned at a distal end portion of a humerus or a tibia, or at a proximal or at a distal end portion of a femur.

In general, the proximal end of the bone is the end of the bone being oriented toward the heart of the human body. The distal end of the bone is the end of the bone being oriented away from the heart of the human body. An intramedullary nail may be a femur nail, a humerus nail or a tibia nail, wherein the intramedullary nail comprises a non-driving end and a driving end. The non-driving end is the end of the nail which firstly enters the intramedullary channel of a bone. Entering the bone from the proximal end of the bone is denoted as antegrade insertion. Entering the bone from the distal end of the bone is denoted as retrograde insertion. Consequently, a nail adapted to be implanted from the proximal end of the tibia may be denoted as antegrade tibia nail, a nail adapted to be implanted from the distal end of the femur may be denoted as retrograde femur nail, a nail adapted to be implanted from the proximal end of the femur may be denoted as antegrade femur nail, and a nail adapted to be implanted from the proximal end of the humerus may be denoted as antegrade humerus nail.

As of today, locking of the non-driven end of intramedullary nails is problematic, namely because of the amount of radiation required during the determination of the position and orientation of transverse locking holes formed within the portion of the intramedullary nail when located in a marrow channel of a bone, to be able to insert locking screws through these holes. Furthermore, it is time consuming and ideally requires well-trained and experienced personal. Therefore, it has a significant influence of the overall operation room time required.

Currently, the situation is the following: A different locking pattern of the non-driving end portion of an intramedullary nail exists for each one of different nails, e.g. humerus, tibia, femur nails. Locking of the non-driving end portion of an intramedullary nail is performed mostly freehand.

U.S. Pat. No. 6,547,791 B1 discloses a tibia nail for retrograde implantation, comprising a tube with a continuous longitudinal bore and including a first anchoring portion with several cross-bores at its non-driving end portion, an adjoining connecting portion, a shank and a second anchoring portion at its driving end portion. The arrangement of the cross-bores permits to fix several fragments at their positions in the region of the tibia plateau, i.e. at the proximal end portion of the tibia.

BRIEF SUMMARY OF THE INVENTION

It may be seen as a need to make locking of the non-driving end portion of intramedullary nails easier. In general, it is of interest to shorten the operation room time which is beneficial not only for the patient under anaesthesia, but ultimately reduces costs.

This is achieved by the subject-matter of each of the independent claims. Further embodiments are described in the respective dependent claims.

In general, an intramedullary nail according to the invention comprises a driving end portion and a non-driving end portion with a longitudinal axis. The non-driving end portion comprises a locking hole arrangement with four holes, i.e. a first hole, a second hole, a third hole, and a fourth hole. The four holes are arranged as a sequence from the non-driving end of the intramedullary nail in a direction to the driving end of the nail, with the first hole arranged closer to the non-driving end than the second hole, the second hole arranged closer to the non-driving end than the third hole, and the third hole arranged closer to the non-driving end than the fourth hole. The first hole and the fourth hole have a corresponding first orientation and the second hole and the third hole have a corresponding second orientation.

According to an embodiment of the invention, the first orientation is a medio-lateral orientation and the second orientation is an anterior-posterior orientation. The medio-lateral orientation and the anterior-posterior orientation are substantially orthogonal with respect to each other.

Due to inaccuracies in determining the respective directions/orientations relative to a human body, orthogonal may include in this context an angle between 80 and 100 degrees.

It is noted that the orientation of the first and fourth holes of the locking hole arrangement at the non-driving end portion of the intramedullary nail may also be different to orthogonal relative to the orientation of the second and third holes, as long as this orientation is well defined and, thus, known. For example, the orientation may be 60 degrees or may be 45 degrees.

According to an embodiment of the invention, the first, second, third and fourth holes are respectively adapted for receiving a locking screw.

Such an arrangement of locking holes may be particularly usable at a non-driving end portion of an antegrade humerus nail, an antegrade tibia nail, an antegrade femur nail as well as a retrograde femur nail.

According to another embodiment of the invention, at least one of the first hole, the second hole, the third hole and the fourth hole is orthogonally oriented with respect to the longitudinal axis of the non-driving end portion.

It is noted that also an orientation not orthogonally with respect to the longitudinal axis may be provided. It may be, that all holes are inclined in a same way relative to the longitudinal axis, but also that at least one hole is inclined in another way as the other ones.

According to another embodiment of the invention, a distance between a centre axis of the first hole and the centre axis of the second hole corresponds to a distance between a centre axis of the third hole and a centre axis of the fourth hole.

The distances from a non-driving end of the intramedullary nail to a respective centre axis of a hole may be as follows:

A distance from the non-driving end to the centre axis of the first hole may be 4 to 44 mm, preferably 5 mm.

A distance from the non-driving end to the centre axis of the second hole may be 9 to 49 mm, preferably 10 mm.

A distance from the non-driving end to the centre axis of the third hole may be 24 to 64 mm, preferably 25 mm.

A distance from the non-driving end to the centre axis of the fourth hole may be 29 to 69 mm, preferably 30 mm.

According to a further embodiment of the invention, the intramedullary nail comprises a fifth hole, wherein a transponder may be arranged in this fifth hole.

The fifth hole may have the same orientation as the first hole and the fourth hole, and may be centred between the second hole and the third hole, as well as between the first hole and the fourth hole. The distance from the non-driving end of the intramedullary nail to the fifth hole may be 16.5 to 56.5 mm, preferably 17.5 mm.

According to another embodiment of the invention, the five holes are equally spaced from each other.

According to a further embodiment of the invention, the transponder may be adapted for generating a signal with a first preferred radiation direction in which the signal has specific symmetry characteristics, allowing the determination of the orientation of the first preferred radiation direction.

The signal symmetry characteristics may be the characteristics of a dipole. The first preferred direction may be the axis of the dipole. The dipole signal characteristics may be generated by a coil.

Furthermore, the transponder may be adapted for generating a signal being indicative for determining at least one of a spatial position and spatial orientation of the transponder so as to allow determining a respective spatial position and spatial orientation of at least one of the first, second, third and fourth holes, based on a predetermined spatial position and spatial orientation of the respective hole with respect to the transponder.

It is noted that the first preferred radiation direction may be aligned with the orientation, i.e. the centre axis of the fifth hole. A second preferred radiation direction may be orthogonal to the first preferred radiation direction.

According to yet another embodiment of the invention, at least one of the first hole, the second hole, the third hole, the fourth hole and the fifth hole comprises a thread. By means of the thread, a locking screw and alternatively a transponder may be reliably arranged and fixed within one of the holes.

According to another aspect of the invention, a combination of an intramedullary nail, as described above, with a targeting detector is provided, wherein the targeting detector is arranged to detect the signal generating by a transponder at the intramedullary nail.

The targeting detector may further be arranged to detect the orientation of the transponder, wherein the detector is adapted for signalling the correspondence of the orientation of at least one of the first hole, the second hole, the third hole and the fourth hole on the one hand, and a targeting orientation on the other hand, based on a predetermined spatial position and a spatial orientation of the respective first hole, second hole, third hole and fourth hole with respect to the transponder.

According to one embodiment, the targeting detector may be located at a tool for introducing a locking screw, helping a physician to localize the locking hole in the non-driving end portion of the intramedullary nail during a so-called freehand introduction of a locking screw.

On the other hand, the targeting detector may be located at a targeting device having a coupling portion adapted to be coupled to the driving end portion of the intramedullary nail. The targeting device may further comprise a drilling gauge with a drilling axis, for easily introducing a locking screw into a respective locking hole in the non-driving end portion of the intramedullary nail.

U.S. Pat. No. 7,686,818 B2, the disclosure of which is incorporated herein by reference, relates to a locking nail and stereotaxic apparatus thereof. Furthermore, US 2008/0170473 A1 the disclosure of which is also incorporated herein by reference, relates to a targeting system. These documents especially provide information concerning exemplary transponders and the use thereof.

The aspects defined above and further aspects, features and advantages of the present invention can also be derived from the examples of the embodiments to be described hereinafter and are explained with reference to examples of the embodiments to which the invention is not limited.

BRIEF DESCRIPTION OF THE DRAWINGS

The invention will now be detailed by way of an exemplary embodiment with reference to the attached drawings.

FIG. 2 is a side view of an intramedullary nail according to the invention.

FIG. 3 is a section view of the end portion of the intramedullary nail according to the invention.

It is noted that the illustration in the drawings is only schematically and not to scale. In different figures, similar elements are provided with the same reference signs.

DETAILED DESCRIPTION

Figure 1:
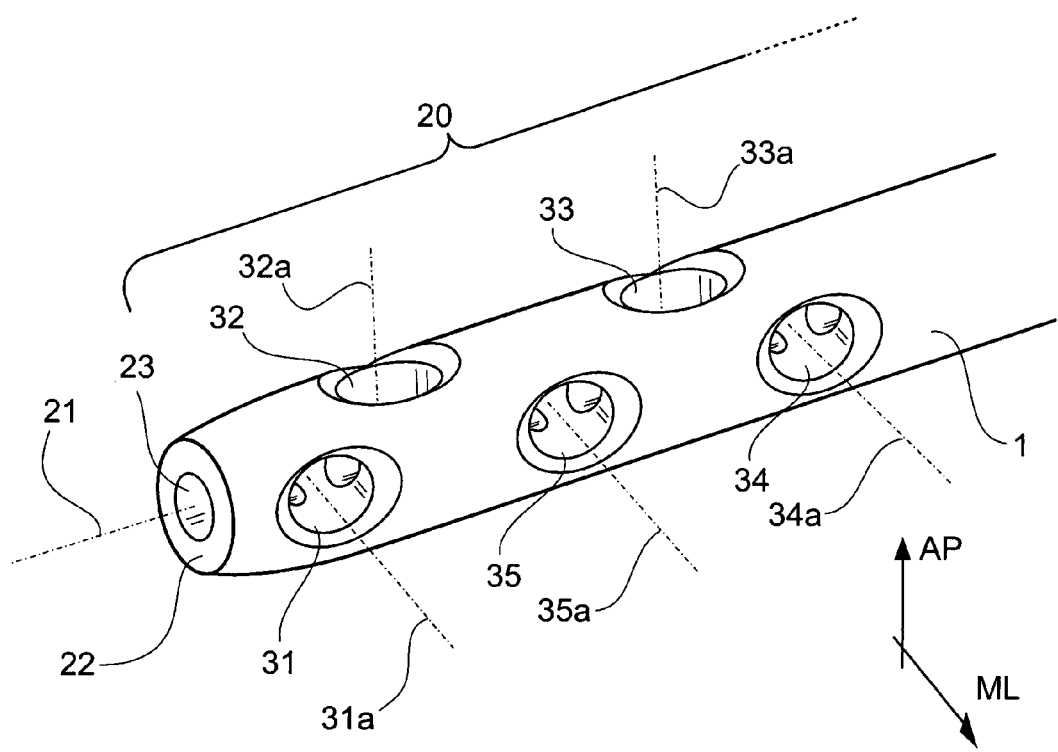
FIG. 1 illustrates an isometric view of an end portion of an intramedullary nail according to the invention.

FIG. 1 is an isometric view of a non-driving end portion 20 of an intramedullary nail 1. The non-driving end portion 20 includes a longitudinal axis 21, a non-driving end 22 and a longitudinal bore 23 arranged substantially parallel to the longitudinal axis 21. The non-driving end 22 is formed as a blunt end of the intramedullary nail 1. Furthermore, five holes are illustrated in FIG. 1. Starting from the non-driving end 22 of the non-driving end portion 20, the intramedullary nail 1 comprises a first hole 31 with a centre axis 31a, a second hole 32 with a centre axis 32a, a fifth hole 35 with a centre axis 35a, a third hole 33 with a centre axis 33a, and a fourth hole 34 with a centre axis 34a. As can be seen, the first hole 31, the fifth hole 35 and the fourth hole 34 are orientated in a first orientation, and the second hole 32 and the third hole 33 are orientated in a second orientation.

Each of the centre axes of the holes is oriented orthogonal to the longitudinal axis 21. Furthermore, the first hole 31 and the fourth hole 34 are orientated orthogonal to the second hole 32 and the third hole 33. The fifth hole 35 is arranged in the middle between the first and fourth holes, orientated in the same direction as the first and fourth holes. The fifth hole 35 is adapted for receiving a transponder. Additionally, in FIG. 1 the directions medio-lateral ML and anterior-posterior AP are illustrated.

FIG. 2 is a side view of the intramedullary nail in the medio-lateral direction. As depict in FIG. 2, a transponder 50 may be arranged in the fifth hole, in the middle between the first hole 31 and the fourth hole 34. In this embodiment, the visual part of the transponder has a greater diameter than the respective diameter of the first and fourth holes.

Further illustrated in FIG. 2 are the distances between some of the centre axes of the holes. The distance between the centre axis of the first hole 31 and the centre axis of the fourth hole 34 is indicated as d1. The distance between the centre axis of the first hole 31 and the centre axis 32a of the second hole 32, as well as the distance between the centre axis 33a of the third hole 33 and the centre axis of the fourth hole 34 is indicated as d2, that is, the distance between the centre axes of the first and second holes is equal to that of the third and fourth holes. The distance between the centre axis of the fourth hole 34 and the centre axis of the fifth hole with the transponder 50 is indicated as d1/2, that is, the transponder is arranged in the middle between the first and fourth holes.

For the sake of completeness, a driving end portion 10 of the intramedullary nails 1 is illustrated in FIG. 2. It is noted that the driving end portion 10 may have any shape or size, depending as to whether the intramedullary nail 1 should be used as humerus nail, as tibia nail or as femur nail.

FIG. 3 is a section view of the non-driving end portion 20 along the plane A-A of FIG. 2. As can be seen in FIG. 3, the intramedullary nail 1 has a hollow shaft (due to the longitudinal bore 23) with a longitudinal axis 21 at its non-driving end portion 20. Also in this figure, the first, fourth and fifth hole are illustrated parallel to each other and in a first orientation, within the plane of the figure, and the second and third holes are illustrated parallel to each other and in a second orientation, perpendicular to the plane of the figure.

Figure 4:
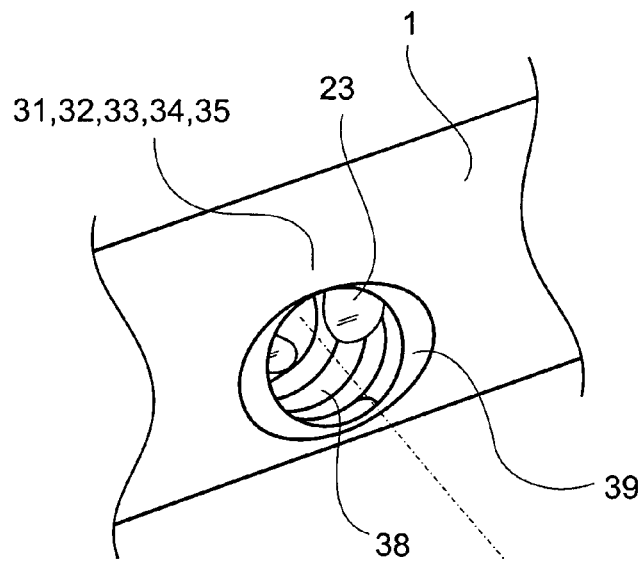
FIG. 4 is an isometric view of a hole including a thread according to the invention.

FIG. 4 is an isometric view showing, in detail, one of the holes 31, 32, 33, 34 and 35 of the non-driving end portion of the intramedullary nail 1. The hole in FIG. 4 includes a thread 38 and a chamfer 39. The chamfer 39 may facilitate an introduction of a screw or of a transponder into the hole.

It will be understood that the thread 38 may be provided in only one of or at least one of as well as in every one of the holes in the non-driving end portion of the intramedullary nail. As also depict in FIGS. 1, 2 and 3, the holes may also comprise only a chamfer 39 and no thread 38.

Figure 5:
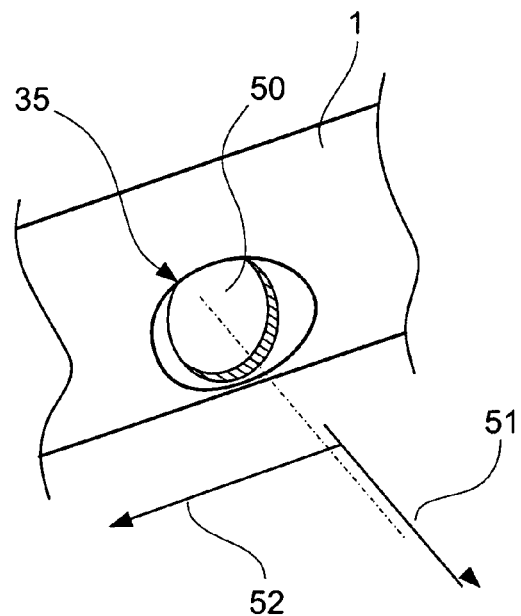
FIG. 5 is an isometric view of a hole including a transponder according to the invention.

FIG. 5 is a detailed view of the fifth hole 35 with a transponder 50 located within the fifth hole. Additionally, a first preferred radiation direction 51 of the transponder 50 and a second preferred radiation direction 52 of the transponder 50 are illustrated. The first preferred radiation direction 51 is substantially aligned with the centre axis of the fifth hole 35 and thus with the centre axis of the transponder 50. The second preferred radiation direction 52 is orientated orthogonal to the first preferred radiation direction 51. It is noted that the second preferred radiation direction may be within a plane being orthogonal to the first preferred radiation direction.

Figure 6:
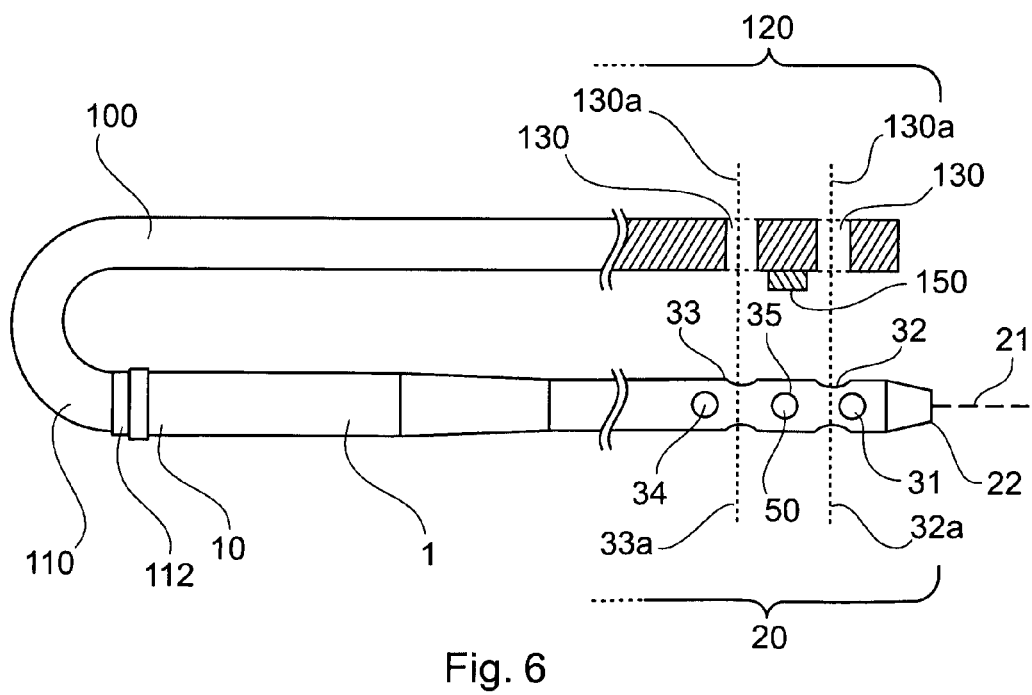
FIG. 6 is a side view of a combination of an intramedullary nail and a targeting device.

FIG. 6 shows a combination of an intramedullary nail 1 together with a targeting device 100, wherein the targeting device 100 includes a portion 110 with a coupling portion 112, wherein the coupling portion 112 may be adapted to be coupled to the driving end portion 10 of the intramedullary nail 1. Furthermore, the targeting device 100 comprises a portion 120 including at least one drilling gauge 130 with a drilling axis 130a.

The targeting device 100 is dimensioned so that the drilling axis of one of the drilling gauges 130 is aligned with, for example, the centre axis 33a of the third hole 33, and that the drilling axis of another one of the drilling gauges 130 is aligned with the centre axis 32a of the second hole 32.

The targeting device 100 may further comprise a targeting detector 150 arranged in a known relation to the holes of the non-driving end portion of the intramedullary nail, so that the targeting detector 150 may receive signals from the transponder 50 to be able to indicate the relative position of the respective drilling gauge relative to one of the holes of the locking hole arrangement in the non-driving end portion 20 of the intramedullary nail 1.

It will be understood, that the targeting device 100 may also be orientated relative to the intramedullary nail so that drilling gauges may be aligned with the first or the fourth hole in the intramedullary nail.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practising the claimed invention, from the study of the drawings, the disclosure and the appended claims. In the claims, the word "comprising" does not exclude other elements and indefinite article "a" or "an" does not exclude a plurality. The mere fact that certain measures are recited in mutual different dependent claims does not indicate that a combination of these measures cannot be used to advantage. Any reference signs in the claims should not be construed as limiting the scope.

LIST OF REFERENCE SIGNS 1 intramedullary nail
10 driving end portion
20 non-driving end portion
21 longitudinal axis of non-driving end portion
22 non-driven end
23 longitudinal bore
31 first hole
31a centre axis of the first hole
32 second hole
32a centre axis of the second hole
33 third hole
33a centre axis of the third hole
34 fourth hole
34a centre axis of the fourth hole
35 fifth hole
35a centre axis of the fifth hole
38 thread
39 chamfer
50 transponder
51 first radiation direction
52 second radiation direction
100 targeting device
110 first portion
112 coupling portion
120 second portion
130 drilling gauge
130a drilling axis
150 targeting detector
AP anterior-posterior
ML medio-lateral
d1, d2 distance

The invention claimed is:
1. An intramedullary nail, comprising
a driving end portion, and
a non-driving end portion having a longitudinal axis,
wherein the non-driving end portion comprises a locking hole arrangement with a first hole, a second hole, a third hole and a fourth hole all having a center axis intersecting the longitudinal axis,
wherein the first hole is arranged closer to a non-driving end of the intramedullary nail than the second hole, the second hole is arranged closer to the non-driving end than the third hole, and the third hole is arranged closer to the non-driving end than the fourth hole,
wherein the first hole and the fourth hole have a corresponding first orientation with respect to a circumference of the nail and the second hole and the third hole have a corresponding second orientation with respect to the circumference of the nail different than the first orientation, and wherein a distance between the center axis of the first hole and the center axis of the second hole is equal to a distance between the center axis of the third hole and the center axis of the fourth hole.

2. The intramedullary nail according to claim 1, wherein the first orientation is a medio-lateral (ML) orientation and the second orientation is an anterior-posterior (AP) orientation.

3. The intramedullary nail according to claim 1, wherein the first hole, the second hole, the third hole and the fourth hole are adapted for receiving a distal locking screw.

4. The intramedullary nail according to claim 1, wherein at least one of the first hole, the second hole, the third hole and the fourth hole being orthogonally oriented with respect to the longitudinal axis of the non-driving end portion.

5. The intramedullary nail according to claim 1, wherein the distance from a non-driving end of the intramedullary nail to:
the center axis of the first hole is 4 to 44 mm,
the center axis of the second hole is 9 to 49 mm,
the center axis of the third hole is 24 to 64 mm, and
the center axis of the fourth hole is 29 to 69 mm.

6. The intramedullary nail according to claim 1, further comprising a fifth hole.

7. The intramedullary nail according to claim 6, wherein at least one of the first hole, the second hole, the third hole, the fourth hole and the fifth hole comprises a thread.

8. The intramedullary nail according to claim 6, wherein the fifth hole has the same orientation as the first hole and the fourth hole and being arranged half the way between the second hole and the third hole.

9. The intramedullary nail according to claim 6, wherein the distance from the non-driving end of the intramedullary nail to the fifth hole is 16.5 to 56.5 mm.

10. The intramedullary nail according to claim 1, further comprising a transponder.

11. The intramedullary nail according to claim 10, wherein the transponder is arranged in a fifth hole.

12. The intramedullary nail according to claim 10, wherein the transponder is adapted for generating a signal wherein the transponder has a first preferred radiation direction, in which first preferred radiation direction the signal has symmetry characteristics, allowing determining the orientation of the first preferred radiation direction.

13. The intramedullary nail according to claim 12, wherein the first preferred radiation direction aligns with the orientation of a fifth hole.

14. The intramedullary nail according to claim 10, wherein the transponder is adapted for generating a signal being indicative for determining at least one of a spatial position and spatial orientation of the transponder so as to allow determining a respective spatial position and spatial orientation of at least one of the first hole, the second hole, the third hole and the fourth hole based on a predetermined spatial position and spatial orientation of the respective first hole, second hole, third hole, and fourth hole with respect to the transponder.

15. The intramedullary nail of claim 1, wherein the distance between the center axes of the second and third holes is greater than the distance between the center axes of the first and second holes.

16. A system comprising the intramedullary nail according to claim 10 and a targeting detector, wherein the targeting detector is arranged to detect the signal generated by the transponder.

17. The system according to claim 16, wherein the targeting detector is adapted to being temporarily fixed to the intramedullary nail via a coupling device.

18. The system according to claim 16, wherein the detector is arranged to detect the orientation of the transponder, wherein the detector is adapted for signaling the correspondence of the orientation of at least one of the first hole, the second hole, the third hole and the fourth hole and a targeting orientation, based on a predetermined spatial position and spatial orientation of the respective first hole, second hole, third hole, and fourth hole with respect to the transponder.

19. An intramedullary nail, comprising:
a driving end portion;
a non-driving end portion having a longitudinal axis;
wherein the non-driving end portion comprises a locking hole arrangement with a first hole, a second hole, a third hole and a fourth hole;
wherein the first hole is arranged closer to a non-driving end of the intramedullary nail than the second hole, the second hole is arranged closer to the non-driving end then the third hole, and the third hole is arranged closer to the non-driving end then the fourth hole;
wherein the first hole and the fourth hole have the same first angular orientation with respect to the longitudinal axis in first and second parallel transverse planes through the circumference of the nail and the second hole and the third hole have the same angular second orientation with respect to the longitudinal axis in third and fourth parallel transverse planes parallel to the first and second transverse planes through the circumference of the nail, the first angular orientation different that the second angular orientation,
wherein a distance between a center axis of the first hole and a center axis of the second hole is equal to a distance between a center axis of the third hole and a center axis of the fourth hole, and
wherein the first orientation is a medio-lateral (ML) orientation and the second orientation is an anterior-posterior (AP) orientation.

20. The intramedullary nail according to claim 19, wherein each of the first hole, the second hole, the third hole and the fourth hole are orthogonally oriented with respect to the longitudinal axis of the non-driving end portion.

* * * * *